US011477967B2

(12) United States Patent
Lockery

(10) Patent No.: US 11,477,967 B2
(45) Date of Patent: Oct. 25, 2022

(54) MICROFLUIDIC DEVICE, SYSTEM AND METHODS THEREOF FOR MEASURING AND RECORDING ELECTRICAL SIGNALS FROM A POOL OF MULTIPLE NEMATODES

(71) Applicants: NemaMetrix Inc., Eugene, OR (US); University of Oregon, Eugene, OR (US)

(72) Inventor: Shawn Lockery, Eugene, OR (US)

(73) Assignees: NemaMetrix Inc., Eugene, OR (US); University of Oregon, Eugene, OR (US)

( * ) Notice: Subject to any disclaimer, the term of this patent is extended or adjusted under 35 U.S.C. 154(b) by 536 days.

(21) Appl. No.: 16/449,438

(22) Filed: Jun. 23, 2019

(65) Prior Publication Data
US 2019/0387717 A1    Dec. 26, 2019

Related U.S. Application Data

(60) Provisional application No. 62/689,052, filed on Jun. 22, 2018.

(51) Int. Cl.
*A01K 67/00* (2006.01)
*A01K 29/00* (2006.01)
*A01K 67/033* (2006.01)
*A61D 3/00* (2006.01)
*G01N 33/50* (2006.01)
*A61B 5/00* (2006.01)
*G01N 27/02* (2006.01)

(52) U.S. Cl.
CPC ........ *A01K 29/005* (2013.01); *A01K 67/0336* (2013.01); *A61B 5/0004* (2013.01); *A61D 3/00* (2013.01); *G01N 27/02* (2013.01); *G01N 33/5085* (2013.01); *A01K 2227/703* (2013.01); *A01K 2267/0393* (2013.01)

(58) Field of Classification Search
CPC .............................. C12M 23/16; B01L 3/5027
See application file for complete search history.

(56) References Cited

U.S. PATENT DOCUMENTS

| 9,723,817 | B2* | 8/2017 | Lockery | G01N 27/02 |
| 2013/0118411 | A1* | 5/2013 | Lockery | G01N 33/5085 |
| | | | | 324/715 |
| 2016/0016169 | A1* | 1/2016 | Ben-Yakar | B01L 3/502738 |
| | | | | 506/40 |

FOREIGN PATENT DOCUMENTS

WO   WO-2019165128 A1 *  8/2019  ......... A01K 67/0336

OTHER PUBLICATIONS

Raizen and Avery. Neuron 12(3):483-495 (Year: 1994).*
Russell et al. J Gerontol A Biol Sci Med Sci, 2019, vol. 74, No. 8, 1173-1179 (Year: 2019).*
Lockery et al. Lab Chip 21(12):2211-2220 (Year: 2012).*

* cited by examiner

*Primary Examiner* — Marcia S Noble
(74) *Attorney, Agent, or Firm* — Koren Anderson

(57) ABSTRACT

The present disclosure provides a microfluidic device and system for measuring a composite electropharyngeogram (EPG) signal from a pool of multiple nematodes, wherein the composite EPG signal is measured from the pool of nematodes present in a single recording channel connected to two or more integrated electrodes. The microfluidic device includes an inlet port and outlet port directly connected to a single recording channel and two or more electrodes directly connected to the recording channel. The recording channel is configured to hold 10 to 10,000 nematodes.

8 Claims, 7 Drawing Sheets

MICROFLUIDIC DEVICE, SYSTEM AND METHODS THEREOF FOR MEASURING AND RECORDING ELECTRICAL SIGNALS FROM A POOL OF MULTIPLE NEMATODES

CROSS-REFERENCE TO RELATED APPLICATIONS

This application claims the benefit of U.S. Provisional Patent Application No. 62/689,052, filed on 22 Jun. 2018, the content of which is incorporated herein by reference in its entirety.

STATEMENT REGARDING FEDERALLY SPONSORED RESEARCH OR DEVELOPMENT

This invention was made with government support under MH051383 awarded by National Institutes of Health. The government has certain rights in the invention

FIELD OF THE INVENTION

This application pertains generally to microfluidic devices and methods thereof for measuring and recording composite electropharyngeogram (EPG) signals from a pool of multiple nematodes.

BACKGROUND OF THE INVENTION

Parasitic nematodes are major contributors to disease in humans, livestock, and companion animals. In addition, the non-parasitic nematode *Caenorhabditis elegans* is both a major model organism for basic research in biology and medicine, and a validated screening organism for developing drugs and nematicides to control parasitic species.

The two main measures of nematode health and dysfunction involve quantification of: (i) movements related to locomotion and (ii) muscle contractions associated with feeding. For adequate statistical significance, both measures often require the assessment of tens to hundreds of nematodes per experimental condition, such as when testing different types of drugs. Numerous methods exist for simultaneous quantification of locomotion in hundreds of individual nematodes, for example by tracking them in videos as they crawl across a laboratory substrate. Itskovits E, Levine A, Cohen E, Zaslaver A. A multi-animal tracker for studying complex behaviors. BMC Biol. 2017 Apr. 6; 15(1):29; Swierczek N A, Giles A C, Rankin C H. High-throughput behavioral analysis on *C. elegans*. Kerr R A. Nat Methods. 2011 Jun. 5; 8(7):592-8. However, the only methods for simultaneous quantification of feeding in nematode populations involve either the measurement of food consumption or the accumulation of fluorescently labeled food in the animal. Both approaches are indirect, and neither is capable of quantifying individual swallowing events.

The nematode feeding organ is the pharynx, a rhythmically active muscular pump that sucks nutrients from the environment and passes them into the gut for digestion. Each pharyngeal contraction, called a pump, generates an electrical event that can be recorded by electrodes in electrical contact with the nematode's body. Such a recording is called an electropharyngeogram (EPG). It has been shown that EPGs can be recorded from a single nematode by placing it in tight fitting microfluidic channel filled with a conductive buffer solution that is in contact with electrodes within the channel. See U.S. Pat. No. 9,723,817, herein incorporated by reference. That device, however, only records EPG measurements from individual nematodes, accommodating up to eight nematodes per microfluidic device, and does not provide a high through put means for measuring and recording EPG signals from a large population of nematodes. Lockery S R, Hulme S E, Roberts W M, Robinson K J, Laromaine A, Lindsay T H, Whitesides G M, Weeks J C. A microfluidic device for whole-animal drug screening using electrophysiological measures in the nematode *C. elegans*. Lab Chip. 2012 Jun. 21; 12(12):2211-20.

Others have described alternative methods for simultaneous quantification of feeding in nematode populations. One such method is the bacteria clearance assay, as in Gomez-Amaro R L et al., Measuring Food Intake and Nutrient Absorption in *Caenorhabditis elegans*. Genetics. 2015 June; 200(2):443-54. In that approach, 3-14 nematodes are loaded into micro wells containing a liquid suspension of bacteria. As the nematodes feed, bacteria are removed from the liquid causing a reduction in its optical density. Feeding is quantified as the change in optical density between two time points, normalized to the number of nematodes in the well. Key drawbacks of the bacteria clearance assay include the fact that: i) for accurate normalization, nematodes must be counted accurately as they are added to the microwells, requiring expensive instrumentation or manual loading, ii) the assay is limited to 14 or fewer nematodes per well, a limitation that arises because when the number exceeds 14, changes in optical density per unit time are no longer a linear function of the number of nematodes in the well, and iii) the assay does not measure feeding movements directly.

Moreover, the reliability of the bacteria clearance assay can be compromised by run-to-run variations in the quality of the bacteria preparations, including such properties as bacterial growth phase, which can alter food consumption rates even when pumping rates are unaffected. This discrepancy occurs because in the logarithmic growth phase many bacteria are in a dividing state, making them larger and thus harder to swallow (Gomez-Amaro et al. 2015).

A second method described by others and used to approximate simultaneous quantification of feeding in nematode populations is a fluorescence accumulation method. Boyd et al. Effects of genetic mutations and chemical exposures on *Caenorhabditis elegans* feeding: evaluation of a novel, high-throughput screening assay. PLoS One. 2007 Dec. 5; 2(12). In that method, a population of nematodes is fed a mixture of *E. coli* bacteria and fluorescent microspheres for 15 min. After feeding, nematodes are paralyzed so they can no longer swallow food and the total accumulated fluorescence of each nematode $f_T$ is measured by passing each nematode through a COPAS Biosort, a flow cytometer adapted for use on nematodes. Feeding is quantified for each nematode as $f_T/t$, where t is the time-of-flight of that nematode in the flow cytometer, an approximate measure of nematode length and thus overall size. Use of a flow cytometer can be expensive, e.g. $400,000/instrument or more, and the assay is both an indirect measure of feeding rate and limited to quantifying for a 15-minute feeding period.

Accordingly, there is a need for a device and methods that simultaneously quantifies direct feeding events from a large number of nematodes and that does not require prohibitively expensive equipment to perform.

The instant system provides a direct rather than indirect measure of the feeding rate and provides advantages as compared to known methods and devices. The advantages include: i) quantification of feeding periods that exceed 15 minutes (fluorescence accumulation method limitation); ii) no required knowledge of the number of nematodes in the device (bacteria clearance assay limitation); and, iii) no run to run variability due to variations in bacterial food (bacteria clearance assay limitation).

Provided herein is a microfluidic device, wherein the length and width of the channel are increased to accommodate a population of nematodes, yielding a composite EPG from a pool of multiple nematodes which is the sum of the EPGs from each nematode in the channel. The advantage over known microfluidic devices for recording EPG signals is the ability to record the composite EPG signal from a large number of nematodes in a single EPG recording channel. Recording EPG signals in single-nematode EPG channels critically depends on the seal resistance which forms between the nematode and the channel. We herein demonstrate that the present microfluidic device provides a sufficient seal resistance to obtain useable recordings when the channel is enlarged to accommodate a large population of nematodes.

The device therefore has the potential to accelerate nematode research, including drug and toxicology screening, by vastly increasing the throughput of EPG methodologies.

SUMMARY OF THE INVENTION

Herein are provided devices, systems and methods for measuring a composite electropharyngeogram (EPG) signal from a pool of multiple nematodes. In embodiments, the microfluidic device comprises an inlet port and outlet port directly connected to a holding reservoir, a single recording channel connected in series to the holding reservoir and, two or more integrated electrodes directly connected to the recording channel. In embodiments, the microfluidic system comprises an inlet port and outlet port directly connected to a holding reservoir, a single recording channel connected in series to the holding reservoir, two or more integrated electrodes directly connected to the recording channel, and at least one differential amplifier or at least one voltage-clamp amplifier, wherein the amplifier is connected to an output from the two or more integrated electrodes.

In alternative embodiments, the microfluidic device comprises a) an inlet port and outlet port directly connected to a single recording channel; wherein the single recording channel, configured to hold 10 to 10,000 nematodes; a tube placed in each of the inlet port and outlet port, wherein the tube placed in the outlet port comprises a filter to retain nematodes in the single recording channel; and, two or more electrodes connected to the recording channel. In embodiments, the tubes are metal and function as the electrodes.

In embodiments, the recording channel is configured to hold 10 to 10,000 nematodes. In certain embodiments, the recording channel is 10 mm to 500 mm in length and 10 μm to 500 μm in width. In certain embodiments, the recording channel is 10 mm to 500 mm in length and 10 μm to 1 mm in width. In embodiments, device comprises a silicone polymer, a thermoplastic polymer, an acrylic polymer, or a polycarbonate polymer. In certain embodiments, the thermoplastic polymer comprises poly(methyl methacrylate) (PMMA), polycarbonate (PC), polystyrene (PS), polyvinyl chloride (PVC), polyimide (PI), olefin polymers, cyclic olefin copolymer (COC), cyclic olefin polymer (COP), or cyclic block copolymer (CBC). In certain other embodiments, the silicone polymer comprises a polydimethylsiloxane (PDMS) elastomer.

In embodiments, the pool of nematodes comprises *Caenorhabditis elegans* (*C. elegans*). In certain embodiments, the pool of nematodes comprises parasitic nematodes. In certain other embodiments, the pool of nematodes comprises transgenic or variant nematodes. In embodiments, the nematodes express one or more human genes. In alternative embodiments, the pool of nematodes comprises wild type nematodes.

Disclosed herein are methods for recording a composite electropharyngeogram (EPG) signal from a pool of multiple nematodes and methods for screening test compounds by recording a composite electropharyngeogram (EPG) signal from a pool of multiple nematodes. In embodiments, a method for recording a composite EPG signal comprises introducing the pool of multiple nematodes into the holding reservoir through the inlet port of the microfluidic system, wherein the pool of multiple nematodes is present in an aqueous buffer, moving the pool of multiple nematodes into the single recording channel, measuring electrophysiological signals from the pool of multiple nematodes, and recording the electrophysiological signals as a single composite EPG. In embodiments, the buffer solution comprises serotonin, food, or other stimulant to cause pharyngeal pumping.

In certain embodiments, the methods herein utilize the microfluidic device that does not comprise a holding reservoir, wherein the pool of multiple nematodes is introduced into the single recording channel through the inlet port of the microfluidic system, wherein the pool of multiple nematodes is present in an aqueous buffer solution, measuring electrophysiological signals from the pool of multiple nematodes and, recording the electrophysiological signals as a single composite EPG.

In embodiments, a method for screening a test compound comprises contacting a pool of multiple nematodes with the test compound, measuring and recording a composite EPG signal from the contacted pool of multiple nematodes, comparing the recorded composite EPG to a control composite EPG, and determining if the recorded composite EPG is altered as compared to the control composite EPG, whereby test compounds are screened. In embodiments, determining if the recorded composite EPG is altered comprises determining the power spectrum of the composite EPG, the frequency of the peak power of the composite EPG, the amplitude of the composite EPG, waveform of the composite EPG, or a combination thereof.

In alternative embodiments, a method for screening a test compound utilize the microfluidic device that does not comprise a holding reservoir wherein tubes are placed in each of the inlet port and the outlet port wherein at least the tube in the outlet port comprises a mesh that maintains the nematodes in the recording channel while allowing for exchange or flow of buffer through the recording channel. In embodiments, a method for screening a test compound comprises use of a first buffer and a second buffer, wherein either of the first or second buffer comprises the test compound and the buffer can be exchanged without removing the pool of multiple nematodes from the recording channel.

In certain embodiments, a method for screening a test compound comprises contacting the pool of multiple nematodes with a first buffer, measuring and recording a composite EPG from the first buffer pool of multiple nematodes, perfusing the pool of multiple nematodes with a second buffer (e.g., exchanging the first buffer for the second buffer), measuring and recording a composite EPG from the second buffer pool of multiple nematodes, comparing the recorded composite EPG from the first buffer pool of multiple nematodes to the recorded composite EPG from the second buffer pool of multiple nematodes and, determining if the recorded composite EPG from the first buffer pool of multiple nematodes is altered as compared to the recorded composite EPG from the second buffer pool of multiple nematodes, whereby test compounds are screened, wherein either of the first buffer or second buffer comprises a test compound and the other buffer is a control buffer.

BRIEF DESCRIPTION OF THE DRAWINGS

In the drawings, like numerals describe similar components throughout the several views and different Figure numbers. The drawings illustrate generally, by way of example, but not by way of limitation, various embodiments disclosed herein.

DETAILED DESCRIPTION OF THE INVENTION

Introduction

Provided herein are microfluidic devices, systems, and methods of use thereof for measuring and recording a composite electropharyngeogram (EPG) from a pool of multiple nematodes. The instant microfluidic devices disclosed herein measure and record electrical signals that reveal the average frequency of individual swallowing events simultaneously in populations of nematodes. The present device, system and method are an improvement over microfluidic devices designed to measure and record an EPG from individual nematodes wherein those devices, discussed in the background section, require the placement of individual nematodes into single-nematode EPG channels, each possessing its own electrodes and differential amplifier. The device and system disclosed herein utilize a pool of multiple nematodes placed in a single EPG channel (e.g. recording channel).

Measuring and recording EPG signals in single-nematode EPG channels critically depends on the seal resistance which forms between the nematode and the channel. Unexpectedly, and as demonstrated in Example 2 and shown in FIG. 4, expansion of a recording channel to accommodate a pool of multiple nematodes (e.g., 10 or more) provided sufficient seal resistance to obtain useable recordings (e.g. composite EPGs).

In one embodiment, the microfluidic devices disclosed herein comprise an inlet port and outlet port connected in parallel to a holding reservoir that is connected in series to a recording channel. See FIG. 1. In this embodiment, the pool of nematodes is loaded into the holding reservoir and then moved into the recording channel, such as by concentrating the nematodes via centrifugation.

Figure 5A:
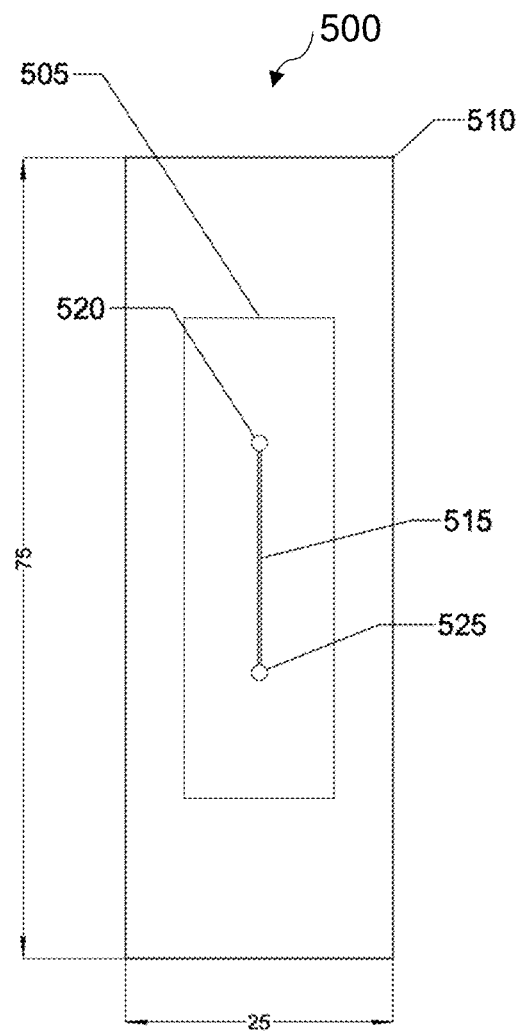
FIG. 5A shows a top view of an exemplary microfluidic device 500. The microfluidic chip 505 includes an inlet port 520 and outlet port 525, connected to a recording channel 515. The microfluidic chip 505 is secured to a backing 510 (e.g. glass plate or microscope slide) to form the microfluidic device 500.
Figure 5B:
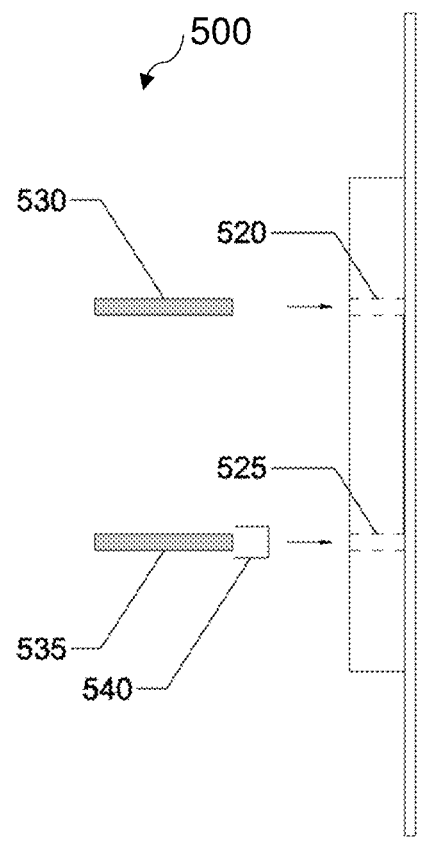
FIG. 5B shows the stainless-steel tubes 530 and 535 in position to be inserted into the inlet port 520 and outlet port 525. A nylon mesh 540 covers the opening of stainless-steel tube 535 inside the microfluidic chip 505.
Figure 5C:
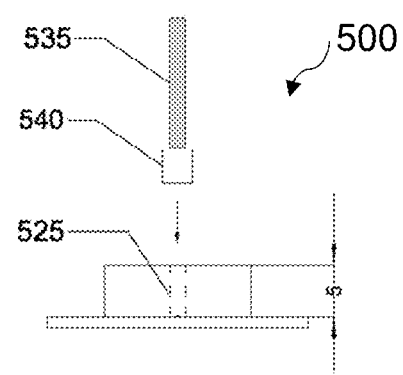
FIG. 5C presents a side view of the microfluidic device 500 with the stainless-steel tube 535 in position to be inserted into the outlet port 525 and the nylon mesh 540 cover the opening of stainless-steel tube.

In certain other embodiments, the microfluidic devices disclosed herein comprise an inlet port and outlet port located at each end of the recoding channel, wherein no holding reservoir is present in this embodiment. The inlet and outlet ports further comprise a tube wherein the end placed in the port comprises a mesh to block and maintain the nematodes in the recording channel. See FIG. 5. In this embodiment, the pool of nematodes is loaded directly in the recording channel via the inlet port, wherein the nematodes remain trapped due to the mesh on the end of the tube in the outlet port. The mesh acts as a filter, making it possible to create a high packing density of nematodes by continuing to inject nematodes until the recording channel is full.

In embodiments, the microfluidic device of FIG. 5 permits perfusion of a test compound during an experiment without removal of nematodes from the recording channel. In certain embodiments, recordings can be obtained before and after perfusion with a test compound, such as a drug candidate, in the same population of nematodes providing methods with internal controls when screening test compounds.

Definitions

As used herein, the terms "a" or "an" are used, as is common in patent documents, to include one or more than one, independent of any other instances or usages of "at least one" or "one or more."

As used herein, the term "or" is used to refer to a nonexclusive or, such that "A or B" includes "A but not B," "B but not A," and "A and B," unless otherwise indicated.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

As used herein, the terms "*Caenorhabditis elegans*" or "*C. elegans*" refer to a free-living transparent nematode, about 1 mm in length, which live in temperate soil environments. The basic anatomy of *C. elegans* includes a mouth, pharynx, intestine, gonad, and collagenous cuticle.

As used herein, the terms "electropharyngeogram" and "EPG" refer to an electrophysiological recording of the pumping activity of the pharynx of an organism (such as a nematode, for example, *C. elegans*). The EPG can be recorded non-invasively with surface electrodes. The waveform of the EPG approximates the derivative of the action potential waveform and includes the E or excitation phase (depolarization of the basal membranes of the pharyngeal muscle cells), the P or plateau phase (membrane potential remains depolarized and muscle contraction occurs), and the R or repolarization phase (return of membrane potential to negative values, muscle relaxation). The E phase includes two closely spaced positive spikes (the corpus and the terminal bulb contractions) and the R phase includes two negative spikes corresponding to relaxation of the corpus and the terminal bulb, respectively. As described throughout the instant specification an EPG recording may not only be obtained for an individual organism but a composite EPG recording may be obtained from a pool of multiple nematodes compacted, for example surface to surface, between two or more electrodes within a recording channel of a microfluidic device. In embodiments, a composite EPG recording may be obtained from a densely packed pool of multiple nematodes arranged between two or more electrodes within a fluid-filled recording channel such that the nematodes occupied at least half the volume of the recording channel between the electrodes.

As used herein, the term "fluidic device" refers to a device that utilizes the flow of fluid to distribute substances and/or organisms (such as substances dissolved in a fluid and/or substances or organisms suspended in a fluid). A fluidic device can be of any dimension, as long as its dimensions are suitable to accommodate the size of substances or organisms included or suspended in the fluid. In embodiments, a device is a microfluidic device that exploits the properties of fluid flow that arise at length scales in the sub-millimeter range. One such property is laminar flow. In some examples, a microfluidic device has a channel or chamber with at least one dimension of 300 microns or less. In other examples, two dimensions are 300 microns or less. Some microfluidic devices are fabricated in glass whereas others are fabricated in a bio-compatible silicone or thermoplastic polymer by replica molding. The latter are referred to as soft-lithography microfluidic devices. The term "microfluidic device" is sometimes used as a synonym for the more general term "microfabricated device," which refers to an object that may or may not exploit the properties of fluid flow at the sub-millimeter scale.

As used herein, the term "nematode" refers to an organism that is a member of the phylum Nematoda, commonly referred to as roundworms. Nematodes include free-living species (such as the soil nematode *C. elegans*) and parasitic species. Species parasitic on humans include ascarids, filarias, hookworms, pinworms, and whipworms. It is estimated that more than two billion people worldwide are infected with at least one nematode species. Parasitic nematodes also infect companion animals and livestock, including dogs and cats (e.g., *Dirofilaria immitis*; heartworm), pigs (*Trichinella spiralis*), and sheep (e.g., *Haemonchus contortus*). There are also nematode species which are parasitic on insects and plants.

As used herein, the term "differential amplifier" refers to a type of electronic amplifier that amplifies the difference between two input voltages but suppresses any voltage common to the two inputs.

As used herein, the term "voltage-clamp amplifier" refers to an amplifier that is used to apply a voltage across a cell or organism while measuring current through the cell or organism. The two-electrode voltage-clamp mode utilizes both a voltage-recording electrode and a current-injecting electrode for the control of membrane voltage.

All publications, patent applications, patents, and other references mentioned herein are incorporated by reference in their entirety for all purposes. In case of conflict, the present specification, including explanations of terms, will control. In addition, the materials, methods, and examples are illustrative only and not intended to be limiting.

Microfluidic Device and System

Provided herein are microfluidic devices, systems, and methods of use for measuring and recording a composite electropharyngeogram (EPG) signal from a pool of multiple nematodes. The disclosed devices allow simultaneous data collection from multiple nematodes, such as 10 or more, in the same recording channel.

In embodiments, a first microfluidic device (e.g. 100) comprises an inlet port and outlet port directly connected to a funnel shaped holding reservoir, a single recording channel connected in series to the holding reservoir and two or more integrated electrodes directly connected to the recording channel. In other embodiments is provided a microfluidic system for measuring and recording a composite electropharyngeogram (EPG) signal from a pool of multiple nematodes, wherein the system comprises an inlet port and outlet port directly connected to a holding reservoir; a single recording channel connected in series to the holding reservoir, two or more integrated electrodes directly connected to the recording channel, and at least one differential amplifier or at least one voltage-clamp amplifier, wherein the amplifier is connected to an output from the two or more integrated electrodes.

In embodiments, the recording channel is configured to hold a pool of multiple nematodes that are present in an aqueous buffer solution. In embodiments, the recording channel is configured to hold 10 to 10,000 nematodes. The pool of multiple nematodes is placed through the inlet port, which is wide enough to accommodate means of transferring an aqueous solution containing the pool of multiple nematodes into the reservoir. In certain embodiments, a syringe or pipette may be used to transfer an aqueous buffer containing the pool of multiple nematodes into the reservoir. In embodiments, the recording channel is configured to accommodate nematodes in various orientations. In certain embodiments, the pool of multiple nematodes is retained in the recording channel by positive pressure.

During use, the recording channel contains an electrically conductive buffer solution (such as a saline solution) which provides electrical continuity between electrodes and the nematodes. In embodiments, the buffer solution further comprises a stimulant that causes or induces pharyngeal pumping. In certain embodiments, the buffer comprises serotonin or nematode food.

In embodiments, the pool of multiple nematodes is packed in between the at least two electrodes that are directly contacted to the recording channel. In embodiments, the recording channel is configured to hold 10 to 10,000 nematodes between the at least two electrodes. In certain embodiments, the microfluidic device comprises a third electrode that is a ground electrode to reduce electrical noise.

In embodiments, electrical contact with the recording channel is achieved by means of electrodes embedded in the material that forms the microfluidic device (such as an integrated electrode). Integrated electrodes can be included in any suitable material (for example, glass, PDMS, polycarbonate, acrylic, or other polymeric material). Integrated electrodes can be fabricated by any means that yields spatially patterned conductive elements that serve as wires. In one non-limiting example, the electrodes are composed of indium tin oxide. In another example, electrodes are composed of metallic silver. Patterning of electrode materials can be achieved for example, using photolithography combined with etching.

In embodiments, a second microfluidic device (e.g., 500) comprises an inlet port and outlet port directly connected by a single fluidic feature, a recording channel located between the inlet and outlet ports molded into the bottom of a block that forms the microfluidic chip, which attached to a backing slip form the microfluidic device, and two electrodes that also function as the inlet and outlet port tube. In certain embodiments, the electrodes are integrated electrodes. In certain other embodiments, metal tubes placed in the inlet port and outlet port function as electrodes. Those tubes, in certain embodiments may comprise a mesh over the end placed in the inlet or outlet port which functions to maintain the nematodes in the recording channel and allows for packing a high density of nematodes in the recording channel. In certain embodiments, a first tube comprising a mesh cover the end is placed the outlet port before nematodes are loaded into the recording channel and a second tube optionally comprising a mesh covering the end is placed in the inlet port after the pool of nematodes are loaded and packed in the recording channel.

In other embodiments is provided a microfluidic system for measuring and recording a composite electropharyngeogram (EPG) signal from a pool of multiple nematodes, wherein the system comprises an inlet port and outlet port directly connected to a recording channel, two integrated electrodes directly connected to the recording channel, at least one differential amplifier, wherein the amplifier is connected to an output from the two integrated electrodes fitted with clips and amplifier cables.

In embodiments, the recording channel of the second microfluidic device is configured to hold a pool of multiple nematodes that are present in an aqueous buffer solution. In embodiments, the pool of multiple nematodes is packed in between the two electrodes within the recording channel. In embodiments, the recording channel is configured to hold 10 to 10,000 nematodes. The pool of multiple nematodes is placed through the inlet port, which is wide enough to accommodate means of transferring an aqueous solution containing the pool of multiple nematodes, into the recording channel. The inlet and outlet ports include a tube-shaped electrode which in the case of the outlet port is covered with a mesh to prevent the nematodes form exiting the recording channel while allowing a buffer solution to pass through the electrode. In certain embodiments, a syringe or pipette may be used to transfer an aqueous buffer containing the pool of multiple nematodes into the recording channel. In embodiments, the recording channel is configured to accommodate nematodes in various orientations. In certain embodiments, the pool of multiple nematodes is retained in the recording channel by positive pressure.

In embodiments, electrical contact with the recording channel is achieved by means of electrodes embedded in the material that forms the microfluidic device (such as an integrated electrode). The electrodes of the second microfluidic device have a dual function. The electrodes fabricated as a hollow tube made of a conducting material function as an electrode and as the lining of the ports for both the inlet and outlet port. In one non-limiting example, the electrodes are composed of stainless-steel. Integrated electrodes can be included in any suitable material used to form the microfluidic chip (for example, glass, PDMS, polycarbonate, acrylic, or other polymeric material).

In certain embodiments, the recording channel, of the first or second microfluidic device, is 10 mm to 500 mm in length and 10 µm to 500 µm in width.

In embodiments, the length of the first or second microfluidic device recording channel is about 10 mm, about 15 mm, about 20 mm, about 35 mm, about 50 nm, about 75 mm, about 100 mm, about 125 mm, about 150 mm, about 200 mm, about 250 mm, about 300 mm, about 350 mm, about 400 mm, about 450 mm or about 500 mm. In certain embodiments, the length of the recording channel is greater than 500 mm. In certain other embodiments, the length of the recording channel is from about 15 mm to about 150 mm, from about 15 mm to about 125 mm, from about 15 mm to about 100 mm, from about 15 mm to about 90 mm, from about 15 mm to about 80 mm, from about 15 mm to about 70 mm, from about 15 mm to about 60 mm, from about 15 mm to about 55 mm, from about 15 mm to about 50 mm, from about 15 mm to about 45 mm, from about 15 mm to about 40 mm, from about 15 mm to about 35 mm, from about 15 mm to about 30 mm, or about 15 mm to about 25 mm. In exemplary embodiments, the length of the recording channel is about 17 mm.

In embodiments, the width of the first or second microfluidic device recording channel is about 10 µm, about 20 µm, about 30 µm, about 40 µm, about 50 µm, about 75 µm, about 100 µm, about 125 µm, about 150 µm, about 175 µm, about 200 µm, about 225 µm, about 250 µm, about 275 µm, about 300 µm, about 325 µm, about 350 µm, about 375 µm, about 400 µm, about 425 µm, about 450 µm, about 475 µm or about 500 µm. In certain embodiments, the width of recording channel is greater about 500 µm. In certain other embodiments, the width of the recording channel is from about 20 µm to about 200 µm, from about 20 µm to about 175 µm, from about 20 µm to about 150 µm, from about 20 µm to about 125 µm, from about 20 µm to about 100 µm, from about 20 µm to about 90 µm, from about 20 µm to about 80 µm, from about 20 µm to about 70 µm, from about 20 µm to about 60 µm, from about 20 µm to about 55 µm, from about 20 µm to about 50 µm, from about 20 µm to about 45 µm, from about 20 µm to about 40 µm or from about 20 µm to about 35 µm. In exemplary embodiments, the width of the recording channel is about 30 µm.

In certain embodiments, a microfluidic device is made from an elastomeric material such as a silicone polymer (for example, poly(dimethyl siloxane) (PDMS)). Suitable PDMS polymers include, but are not limited to Sylgard® 182, Sylgard® 184, and Sylgard® 186 (Dow Corning, Midland, Mich.). In one non-limiting example, the PDMS is Sylgard® 184. Additional polymers that can be used to make the disclosed microfluidic chip include acrylic, polyurethane, polyamides, polyethelyene, polycarbonates, polyacetylenes and polydiacetylenes, polyphosphazenes, polysiloxanes, polyolefins, polyesters (such as thermoset polyester (TPE)), polyethers, poly(ether ketones), poly(alkaline oxides), poly (ethylene terephthalate), poly(methyl methacrylate), polyurethane methacrylate (PUMA), polystyrene, thiol-enes, fluoropolymers (for example, perfluoropolyethers), Norland Optical Adhesive 81, and derivatives and block, random, radial, linear, or teleblock copolymers, cross-linkable materials such as proteinaceous materials and/or combinations of two or more thereof. Also suitable are polymers formed from monomeric alkylacrylates, alkylmethacrylates, alpha-methylstyrene, vinyl chloride and other halogen-containing monomers, maleic anhydride, acrylic acid, and acrylonitrile. Monomers can be used alone, or mixtures of different monomers can be used to form homopolymers and copolymers. See, e.g., U.S. Pat. No. 6,645,432; McDonald et al., *Electrophoresis* 21:27-30, 2000; Rolland et al., *J. Am. Chem. Soc.* 126:2322-2323, 2004; Carlborg et al., *Lab Chip* 11:3136-3147, 2011; Sollier et al., *Lab Chip* 11:3752-3765, 2011. In some examples, the channel of the device (such as a device made from PDMS) can be coated with a sol-gel. See Abate et al., *Lab Chip* 8:516-518, 2008, for example. In other embodiments, suitable materials for making the disclosed microfluidic device include polymeric films, photoresist, hydrogels, or thermoplastic polymers.

In certain embodiments, a present first or second microfluidic device comprises a silicone polymer, thermoplastic polymer, an acrylic polymer, or a polycarbonate polymer. In exemplary embodiments, a silicone polymer comprises polydimethylsiloxane (PDMS) elastomer. In certain other embodiments, the thermoplastic polymers comprise poly (methyl methacrylate) (PMMA), polycarbonate (PC), polystyrene (PS), polyvinyl chloride (PVC), polyimide (PI), olefin polymers, cyclic olefin copolymer (COC), cyclic olefin polymer (COP), or cyclic block copolymer (CBC). In exemplary embodiments, the microfluidic device comprises PDMS.

Microfluidic devices can be fabricated by methods known to one of ordinary skill in the art. In some embodiments, the disclosed devices are made by molding uncured polymer from a photoresist master using standard photolithographic methods (e.g., U.S. Pat. No. 6,645,432; Madou, *Fundamentals of Microfabrication*, CRC Press, Boca Raton, Fla., 1997). In other embodiments, the disclosed devices are made by chemical etching, laser cutting, photopolymerization, lamination, embossing, or injection molding. In the case of glass devices, the microfluidic device can for instance be fabricated by etching the various types of channels into a thin glass plate and bonding this plate to a second glass plate that serves as a flat substrate. One of ordinary skill in the art can select an appropriate fabrication method based on the selected material for the device.

Figure 1:
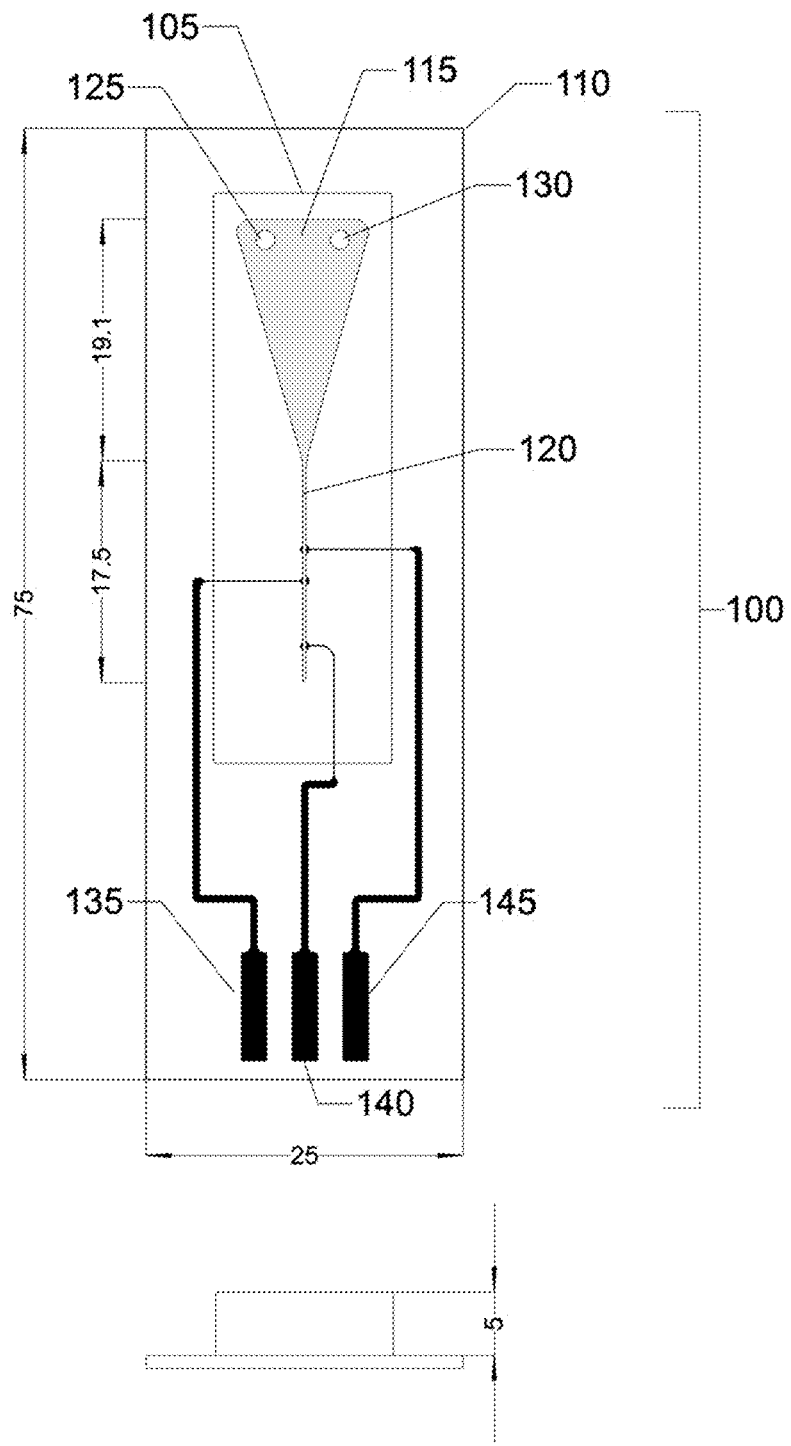
FIG. 1 shows a top view and an end view of an exemplary microfluidic device 100. The microfluidic chip 105 includes an inlet port 125 and outlet port 130, connected in parallel to a reservoir 115, that is connected in series to a recording channel 120 wherein three electrodes 135, 140 (ground electrode) and 145 are connected to the recording channel 120. The microfluidic chip 105 is secured to a backing 110 (e.g. glass plate or microscope slide) to form the microfluidic device 100.

FIG. 1 is a top view of one embodiment of the first microfluidic device 100. The device includes the microfluidic chip 105 and a backing 110, wherein the chip 105 includes an inlet port 125, an outlet port 130, each connected to a reservoir 115 that is connected in series to a recording channel 120. The electrodes, 135, 140 and 145, are directly connected to the recording channel. An aqueous buffer comprising the pool of multiple nematodes flows from the inlet port 125, into the reservoir 115 and the recording channel 120, wherein the electrical signal from the pool of multiple nematodes is recorded for those nematodes between electrodes 135 and 145; electrode 140 is a ground that reduces electrical noise. To aid in movement of nematodes into the recording channel 120, in certain embodiments, the microfluidic device 100 is subjected to a spin that forces buffer solution and nematodes into the recording channel 120. See Table 1 and A for exemplary dimensions of the microfluidic device 100.

In embodiments, the microfluidic device comprises a range of dimension measurements. No limitation on the length or width of recoding channel 120 is intended wherein the dimensions inform the dimension of the reservoir 115 and together the reservoir 115 and recording channel 120 define the outer dimensions of the microfluidic chip 105 and microfluidic device.

TABLE A

Range of dimension measurement for microfluidic device 100

| Feature | Width (mm) | Length (mm) | Depth (mm) |
|---|---|---|---|
| Inlet port (125) | 1-2 (diam) | 1-2 (diam) | Depth of chip |
| Outlet port (130) | 1-2 (diam) | 1-2 (diam) | Depth of chip |
| Holding reservoir (115) | 10-50 | 10-50 | 0.01-0.30 |
| Recording channel (120) | 0.01-1 | 5-500 | 0.01-0.30 |
| Chip (PDMS block) (105) | 20-60 | 25-160 | 1-10 |

Exemplary depth of chip 105 dimensions is about 5 mm. See FIG. 1.

Figure 2:
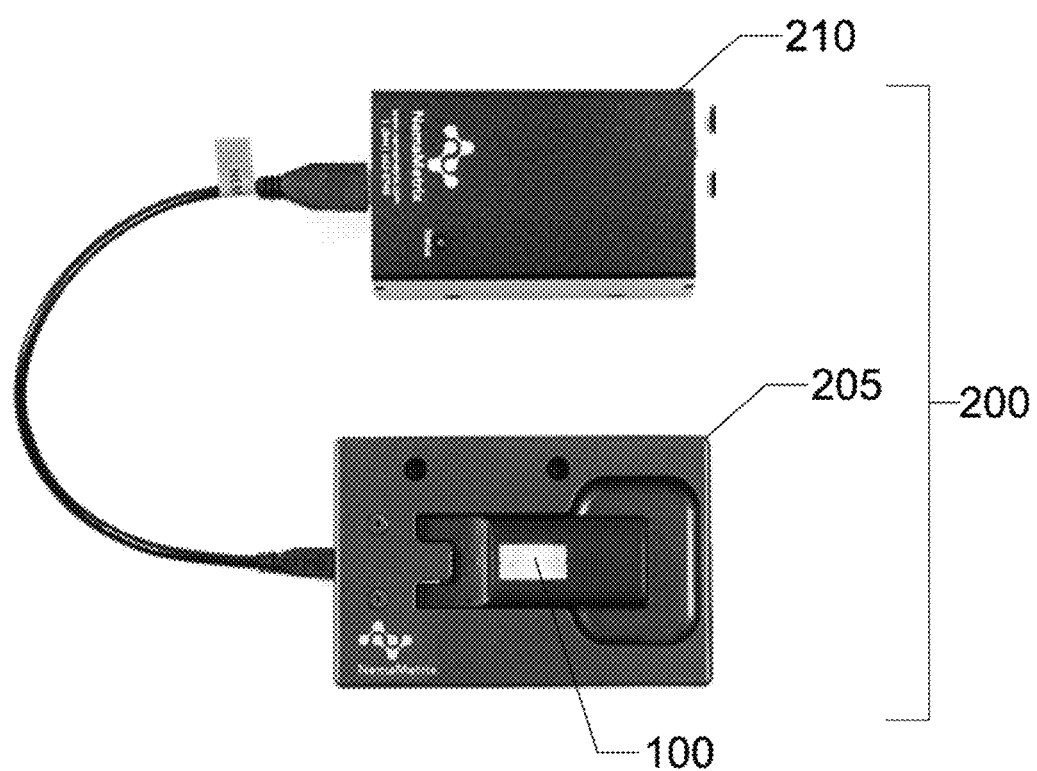
FIG. 2 shows a top view of an exemplary microfluidic system 200 that includes the microfluidic device 100 placed in a recording dock 205 that is connected to a differential amplifier 210.

FIG. 2 is an image of an exemplary microfluidic system 200. The system includes the microfluidic device 100 loaded in a recording dock 205 and connected to a differential amplifier 210. In certain embodiments, the recording dock is connected to a voltage-clamp amplifier.

FIGS. 5A-5C and 6 provide a view of the second microfluidic device 500 and system 600. A microfluidic chip 505 bonded to a backing 510 contains a single fluidic feature, a recording channel 515, molded into the bottom of the chip. The channel is connected to an inlet port 520, and an outlet port 525. Two metal tubes 530 and 535 form inlet 520 and outlet 525 connections, respectively. The opening of the tube 535 is covered by a mesh 540. The stainless-steel tubes 530, 535 contact the aqueous solution in the channel such that they also served as electrodes.

See Table 4 and A for exemplary dimensions of the microfluidic device 500.

TABLE 4

Dimensions of the Exemplary Microfluidic Device 500 of FIG. 5

| Feature | Width (mm) Top view x-dimension | Length (mm) Top view y-dimension | Depth (mm) |
|---|---|---|---|
| Inlet port (520) | 1-2 (diam) | 1-2 (diam) | 5 |
| Outlet port (525) | 1-2 (diam) | 1-2 (diam) | 5 |
| Stainless-steel tubes (530, 535) | 1-2 (diam) | 1-2 (diam) | 12.5 |
| Recording channel (515) | 0.01-1 | 5-500 | 0.01-0.30 |
| Chip (PDMS block) (505) | 20-60 | 25-160 | 1-10 |

Figure 6:
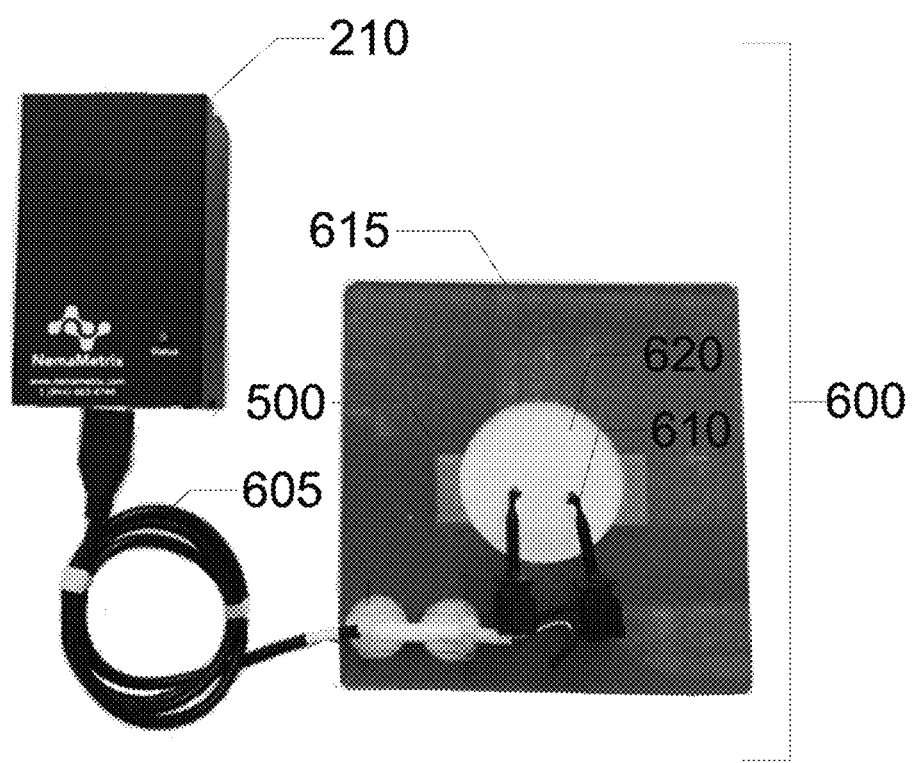
FIG. 6 shows a top view of an exemplary microfluidic system 600 that includes the microfluidic device 500 that is connected to a differential amplifier 210, and amplifier cable 605 fitted with clips 610 to connect the amplifier 210 to the microfluidic device 500.

FIG. 6 is an image of an exemplary microfluidic system 600. The system includes microfluidic device 500, differential amplifier 210, amplifier cable 605 fitted with clips 610 to connect the amplifier to the microfluidic device 500.

Methods

Disclosed herein are methods for recording a composite electropharyngeogram (EPG) signal from a pool of multiple nematodes. In embodiments, the method comprises introducing the pool of multiple nematodes into the holding reservoir through the inlet port of a present microfluidic device, wherein the pool of multiple nematodes is present in an aqueous buffer, moving the pool of multiple nematodes into the single recording channel, measuring electrophysiological signals from the pool of multiple nematodes and recording the electrophysiological signals as a single composite EPG.

In some embodiments, the system includes the microfluidic device, two or more electrodes, one or more amplifiers, which are connected to outputs from each electrode, an oscilloscope, which receives input from the amplifier, a data acquisition unit, which receives input from the amplifier; and a computer, which receives input from the data acquisition unit. In some examples, the system also includes a means for regulating flow of solutions through the device (such as a pump, for example, a syringe pump). One of ordinary skill in the art can utilize the systems disclosed herein to measure composite EPG activity of a pool of multiple nematodes. In embodiments the pool of multiple nematodes comprises *C. elegans*. In other embodiments, the pool of nematodes comprises parasitic nematodes.

The nematodes are introduced to the device by any convenient means. In some examples, the nematodes are introduced into the device by transferring the pool of multiple nematodes to the inlet port (which is pre-loaded with an aqueous buffer) and applying gentle pressure (for example, from a syringe) to move the nematodes into the reservoir and the recording channel. In other embodiments, once loaded in the reservoir, the microfluidic device is subjected to centrifugal forces to move the nematodes into the recording channel. In certain embodiments, the cuticle of the nematode is made more permeable to drugs and test compounds by means of chemical treatments and/or genetic mutations. In other embodiments, the ability of the nematode to capture and/or excrete foreign chemicals is compromised by genetic mutation of endogenous pumps and other proteins.

In certain embodiments, when using the second microfluidic device, nematodes maintained in the recording channel allow for exchange or flow of buffer through the recording channel. The nematodes trapped in the recording channel by a mesh over the outlet port can be introduced to a new buffer solution by flushing, from inlet port to outlet port, with a fresh first buffer solution or a second buffer solution. The first or second buffer solution may include a test compound(s). The exchange of buffer solution allows for the screening of test compounds by recording a composite electropharyngeogram (EPG) signal from a pool of multiple nematodes.

Electrical recordings are made using standard techniques known to one of ordinary skill in the art. In some examples, EPGs are recorded by AC differential amplifiers connected to metal electrodes integrated into the device. Signals are displayed on oscilloscopes and recorded for later analysis using a data acquisition system connected to a computer running data acquisition software. Data analysis is performed offline after experiments. Raw EPG recordings can be filtered to remove slow drift and high-frequency noise. Filtered recordings can be subjected to a conventional algorithm, such as the fast Fourier transform, for computing the power spectrum of the recording to identify the average pumping frequency of the pool of nematodes. The power spectrum can be computed as function of time or experimental treatments, including drugs, mutants, and toxic compounds.

Measuring and recording a composite electropharyngeogram (EPG) signal from a pool of multiple nematodes requires a pool of nematodes of a similar size. To obtain nematodes of a consistent size that are compatible with the dimensions of a recording channel, a large number of age synchronized eggs were deposited in a culture plate containing food and cultivated to yield a large population of young adult nematodes. The size of the nematodes can be controlled by selecting the time for incubation. In an exemplary embodiment the eggs were deposited in a culture plate containing food and cultivated at 20° C. for 3 days.

In alternative embodiments, methods using filters can also be used to obtain an age/size synchronized population of nematodes for use in the present methods. See US Patent Publ. No. 2019/0090458.

The nematodes are prepared for recording by suspending the nematodes in a buffer, preferably an M9 buffer solution (See Example 2 for buffer details). To stimulate pharyngeal pumping, the final resuspension buffer used "serotonin M9 buffer solution" which contained 10 mM serotonin in addition to the constituents in Table 3.

In embodiments, the nematodes are injected into the first microfluidic device (100) inlet port (125) filling the reservoir. The microfluidic device (100) is then centrifuged to pack the nematodes into the channel (120). The microfluidic device is inserted into a recording dock 205 thereby connecting it to a differential amplifier 210, which amplified the voltage difference between electrodes 135 and 145 with the third electrode 140 serving as a ground electrode to reduce electrical noise. See Example 2.

In embodiments, the nematodes are injected into the second microfluidic device (500) inlet port (520), suspended in M9 buffer without serotonin, until the channel is filled to capacity, the nematodes being prevented from exiting the channel via the outlet port by the mesh covering the outlet port electrode. The M9 buffer solution is replaced with a second buffer solution, the serotonin containing buffer, by injecting the second buffer into the inlet port until about 10 times the volume of the recording channel exits the outlet port. The microfluidic device electrodes are connected to a differential amplifier 210, using the cords (605) and clip (610) to record the composite EPG. See Example 4.

Disclosed herein are methods for screening test compounds by recording a composite electropharyngeogram (EPG) signal from a pool of multiple nematodes. In embodiments, the method comprises contacting the pool of multiple nematodes with the test compound, measuring and recording a composite EPG from the contacted pool of multiple nematodes, comparing the recorded composite EPG to a control composite EPG, and determining if the recorded composite EPG is altered as compared to the control composite EPG, whereby test compounds are screened.

In embodiments, determining if the recorded composite EPG is altered comprises determining the power spectrum of the composite EPG, the frequency of the peak power of the composite EPG, the amplitude of the composite EPG, waveform of the composite EPG, or a combination thereof. In embodiments, the test compound is selected from a drug, a drug candidate, an industrial chemical, or an environmental pollutant. In certain embodiments, the drug or drug candidate is selected from an organic compound, an inorganic compound, a hormone, a growth factor, a cytokine, a receptor, an antibody, an enzyme, a peptide, an aptamer or a vaccine.

In some embodiments, the disclosed methods include screening for anthelmintic or antimicrobial compounds. In other embodiments, the methods include screening for compounds of use for treating neuromuscular diseases (such as muscular dystrophies, for example, Duchenne muscular dystrophy), neurodegenerative diseases (such as Alzheimer disease, Parkinson disease, Huntington disease, or tauopathies), mitochondrial disorders, or substance abuse disorders.

Methods of screening for or identifying anthelmintic compounds include introducing nematodes (such as *C. elegans*) in a device disclosed herein, contacting the nematode with one or more test compounds, and recording a composite EPG from the nematodes, as disclosed above. The composite EPG in the presence of the one or more test compounds is compared to a control (such as a composite EPG from the same or a different *C. elegans* in the absence of the test compounds) and the compound is identified as an anthelmintic or candidate anthelmintic if the composite EPG is altered (for example, the size and/or frequency of the EPG, or a portion thereof is decreased) in the presence of the test compound as compared to the control. In embodiments, the nematodes are contacted with serotonin or bacterial food prior to and/or concurrent with the test compound to stimulate pharyngeal pumping.

In embodiments, the pool of nematodes comprises: *C. elegans*; parasitic nematodes; transgenic or variant nematodes; nematodes that express one or more human genes; or, wild type nematodes.

Methods of screening for or identifying compounds of potential use for treating disease, such as neurodegenerative disease (for example, Parkinson disease, Huntington disease, Alzheimer disease), neuromuscular disease (for example, spinal muscular atrophies or amyotrophic lateral sclerosis), and muscular degenerative disease (for example, muscular dystrophies or sarcopenia) and/or inhibiting or reducing aging include introducing nematodes (such as *C. elegans*) in a device disclosed herein, contacting the pool of multiple nematodes with one or more test compounds, and recording a composite EPG from the nematodes, as disclosed above. In certain embodiments, such as diseases for which the *C. elegans* genome contains a gene that is orthologous to the human gene implicated in the disease, a strain is created or obtained in which that gene is mutated and is utilized in the screening methods. In embodiments, a strain is created in which the human gene is expressed in *C. elegans* by transgenic techniques. Strains that are disease models can be used in drug screens by searching for compounds that mitigate one or more phenotypes in *C. elegans*. This mitigation can be the result of either chronic or acute exposure to a test compound. In one embodiment, recording a composite EPG signal from the pool of multiple nematodes is used to test for mitigation of disease phenotypes consisting of alterations in the behavior, physiology, and/or other aspects of the pharynx. In one non-limiting example, the *C. elegans* model for spinal muscular atrophy (SMA) exhibits reduced rates of pharyngeal pumping. A candidate compound in a drug screen for SMA is identified by a reduction or reversal of the reduced pumping phenotype as compared to a control group (such as untreated *C. elegans*). In other embodiments, histograms of interspike intervals are used to assess effects of treatments on pumping. In the case of some *C. elegans* disease models, the presence or absence of a pharyngeal phenotype is unknown. In these embodiments, the microfluidic device is used to test for such a phenotype. If a pharyngeal phenotype exists, then the model can be used as above to screen for drugs. Some controls in drug screening experiments would be to apply the test compound to wild type nematodes with the expectation that changes in the pharyngeal phenotype are absent, or in a direction opposite to the change seen in the disease model. For example, a drug effective against SMA might have no effect on wild type nematodes, or it might increase the rate of pharyngeal pumping.

*C. elegans* is well-established as a model in aging research. The devices disclosed herein provide a means of assessing or screening the effects of treatments (for example, genetic alterations, pharmaceutical compounds, and/or environmental conditions) on the process, extent and mechanism of aging. The *C. elegans* pharynx exhibits a decline in pumping rate with increasing age. In some examples, the microfluidic devices are used to quantify the effects of treatments on aging. This is done by growing and maintaining nematodes under conditions of chronic exposure to the treatment and sampling pumping rate throughout the aging process by monitoring pumping rate in a present microfluidic device. Pumping is stimulated by contact with serotonin or bacterial food. In some examples, controls include nematodes of similar ages that were not exposed the treatment.

Many nematode species are parasites of plants causing an estimated $100 billion of worldwide crop losses annually. These nematodes also transmit damaging viruses to plants. Available control measures are very limited, with most plant nematicides withdrawn from the market because of environmental concerns. Many species of plant nematodes have an elaborate feeding apparatus, including a sharp stylet that is rhythmically protruded and retracted to pierce plant cell walls and pump fluids during feeding (Wyss, *Feeding behavior of plant parasitic nematodes* In "The Biology of Nematodes, D. L. Lee, editor, 2002, Taylor and Francis, London). When plant nematodes are contacted with serotonin, this feeding apparatus, which is homologous to the pharynx of non-plant nematodes, emits electrical impulses that can be monitored by conventional EPG recording methods (Rolfe and Perry, *Nematology* 3:31-34, 2001). Many plant nematodes are of a size that is compatible with the present microfluidic devices. Thus, also disclosed herein are methods of assessing or screening the effects of treatments (for example, genetic alterations, pharmaceutical or other compounds, and/or environmental conditions) on plant nematodes utilizing the devices disclosed herein. In some examples, the present microfluidic devices are used to quantify the effects of treatments on feeding in plant nematodes. Pumping is stimulated by contact with serotonin in the device. The nematodes are exposed to the treatment chronically or acutely. In some examples, pumping rate is measured. In other examples, histograms of interspike intervals are used to assess effects of treatments on pumping. Controls include nematodes of the same species and age that are not exposed to the treatment, for instance.

After nematodes, the most abundant parasitic nematodes are digenetic trematodes, also known as flukes or flatworms. They parasitize a broad range of vertebrates, including humans and domestic animals, leading to disease and economic losses. Whereas nematodes have a complete digestive system, with a mouth at one end and an anus at the other, a fluke's mouth leads to a blind sac. However, like nematodes, many flukes have well-developed pharynges, which are used to ingest blood or tissue from hosts. Many species of parasitic and free-living flukes have been the subjects of intense biological inquiry in laboratory settings. As is the case for *C. elegans*, studies of free-living species can inform research on parasitic species. The muscular pharynx is typically richly innervated by neurons containing various neurotransmitters and neuromodulators. For example, dopamine, allatostatin, and octopamine receptors are present in the neural plexus innervating the pharynx of the non-parasitic freshwater flatworm *Schmidtea mediterranea*. In some examples, the EPG devices disclosed herein are used to quantify the effects of drugs and other treatments on feeding in trematodes. Trematodes are introduced into an EPG array that has been modified by adjusting the size of the channels to accommodate them. Pharyngeal activity is stimulated by contacting the animals with an appropriate neurotransmitter. The nematodes are exposed to the treatment chronically or acutely. In some examples, pumping rate is measured. In other examples, histograms of interspike intervals are used to assess effects of treatments on pumping. Controls involve trematodes of the same species and age that are not exposed to the treatment, for instance.

Also disclosed herein are methods of identifying compounds that are toxic or have toxic effects on an organism. In some embodiments, the methods include screening compounds for inhibitors of the HERG channel (for example, potentially cardiotoxic compounds). In other embodiments, the methods include screening compounds for toxicity, for example potential environmental toxicity.

Inhibition of the HERG potassium channel can cause long QT syndrome and potentially fatal ventricular arrhythmias. Several compounds have been withdrawn from late stage clinical trials as a result of cardiotoxicity due to HERG channel inhibition and screening for long QT effects is now mandatory for new drug candidates. Therefore, methods to identify potential HERG channel inhibitors early in drug development can eliminate potentially unsafe compounds prior to significant investment and can streamline development of compounds that do not exhibit cardiotoxicity.

In embodiments, methods of identifying compounds that inhibit the HERG channel include introducing nematodes (such as C. elegans) in a device described herein, contacting the nematodes with one or more test compounds, and recording an EPG from the pool of multiple nematodes, as disclosed above. The composite EPG in the presence of the one or more test compounds is compared to a control (such as a composite EPG from the same or a different C. elegans in the absence of the test compound) and the compound is identified as an inhibitor of HERG if the composite EPG is altered (for example, inhibited) in the presence of the test compound as compared to the control. In some examples, the composite EPG is inhibited (for example, the size and/or frequency of the EPG, or a portion thereof is decreased) in the presence of the test compound as compared to the control. In embodiments, the frequency of action potentials within the composite EPG is increased or reduced indicating, respectively, facilitation or inhibition of the composite EPG. In some examples, the nematodes are contacted with serotonin or bacterial food prior to and/or concurrent with the test compound to stimulate pharyngeal pumping.

Methods of screening for or identifying toxic compounds include introducing a pool of multiple nematodes (such as C. elegans) in a device disclosed herein, contacting the nematodes with one or more test compounds, and recording a composite EPG from the nematodes, as disclosed above. The composite EPG in the presence of the one or more test compounds is compared to a control (such as a composite EPG from the same or a different C. elegans in the absence of the test compound) and the compound is identified as toxic or potentially toxic if the composite EPG is altered (for example, inhibited) in the presence of the test compound as compared to the control. In some examples, the amplitude of action potentials or frequency of action potentials is decreased in the presence of the test compound as compared to the control. In some examples, the nematodes are contacted with serotonin or bacterial food prior to and/or concurrent with the test compound to stimulate pharyngeal pumping. In some examples, the compound is an environmental toxin (such as a heavy metal), pesticide, herbicide, industrial chemical, or naturally occurring compound of interest. Exemplary compounds include, but are not limited to, those listed in the 1989 OSHA Toxic and Hazardous Substances List.

The test compounds used in the present invention include, but are not limited to drugs, drug candidates, biologicals, food components, herb or plant components, proteins, peptides, oligonucleotides, DNA and RNA. In embodiments, the test compound is a drug, a drug candidate, an industrial chemical, an environmental pollutant, a pesticide, an insecticide, a biological chemical, a vaccine preparation, a cytotoxic chemical, a mutagen, a hormone, an inhibitory compound, a chemotherapeutic agent or a chemical. In certain embodiments, the drug or drug candidate is selected from the group consisting of an organic compound, an inorganic compound, a hormone, a growth factor, a cytokine, a reception, an antibody, an enzyme, a peptide, an aptamer or a vaccine. The test compound can be either naturally-occurring or synthetic and can be organic or inorganic. A person skilled in the art will recognize that the test compound can be added to the pool of multiple nematodes and/or the microfluidic device in an appropriate solvent or buffer.

In embodiments, the test compound includes pharmacologically active drugs or drug candidates and genetically active molecules. Test compounds of interest include chemotherapeutic agents, anti-inflammatory agents, hormones or hormone antagonists, ion channel modifiers, and neuroactive agents. Exemplary of pharmaceutical agents suitable for this invention are those described in "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming Organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

In embodiments, the test compound includes all of the classes of molecules disclosed herein and may further or separately comprise samples of unknown content. While many samples will comprise compounds in solution, solid samples that can be dissolved in a suitable solvent may also be assayed. Samples containing test compounds of interest include environmental samples, e.g., ground water, sea water, or mining waste; biological samples, e.g., lysates prepared from crops or tissue samples; manufacturing samples, e.g., time course during preparation of pharmaceuticals; as well as libraries of compounds prepared for analysis; and the like. Samples of interest include test compounds being assessed for potential therapeutic value, e.g., drug candidates from plant or fungal cells.

Test compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, naturally or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification to produce structural analogs.

EXAMPLES

The following examples are put forth so as to provide those of ordinary skill in the art with a complete disclosure and description of how to use the embodiments provided herein and are not intended to limit the scope of the disclosure nor are they intended to represent that the Examples below are all of the experiments or the only experiments performed. Efforts have been made to ensure accuracy with respect to numbers used (e.g. dimensions, amounts, temperature, etc.) but some experimental errors and deviations should be accounted for. Unless indicated otherwise, dimensions are in millimeters (mm), and temperature is in degrees Centigrade. It should be understood that variations in the methods as described can be made without changing the fundamental aspects that the Examples are meant to illustrate.

Example 1: Design and Fabrication of the Microfluidic Device (100)

Provided herein is a microfluidic device and system for measuring and recording a composite electropharyngeogram (EPG) signal from a pool of multiple nematodes. See FIGS. 1 and 2.

Provided herein is the design and fabrication of the microfluidic device 100 and system 200 represented in FIGS. 1 and 2. The microfluidic device was prepared with a rectangular block (e.g. microfluidic chip) 105 composed of polydimethylsiloxane (PDMS) measuring 45 mm×14 mm×5 mm bonded to a 1 mm thick glass microscope slide (e.g. backing) 110 measuring 75 mm×25 mm. Two fluidic features, connected in series, were molded into the bottom of the block: a triangular shaped reservoir 115 which accepts a population of, or a pool of, multiple nematodes suspended in a buffer solution, and a 0.30 mm wide recording channel 120. The reservoir 115 had 1.5 mm diameter inlet port 125 and 1.5 mm diameter outlet port 130. Three electrodes 135, 140 and 145, made contact with any buffer solution filling the recording channel 120. Regions of the electrodes beneath the PDMS block 105 had a high length to width ratio to increase the fluidic resistance of these potential leakage pathways.

The microfluidic device 100 was fabricated using single-layer photo-lithography and single-layer soft-lithography techniques. A photomask containing the microfluidic features 115 (reservoir) and 120 (recording channel) was drawn using Vectorworks 2017 CAD software and printed on a transparency with a resolution of 25,400 dots per inch (CAD/Art Services, Bandon, Oreg.). A 3-inch silicon wafer was spin coated with SU8-2075 photoresist (Microchem Corp.) at 1740 revolutions per minute (RPM) to obtain a height of 100 microns. The coated wafer was exposed to UV light using the photomask. The wafer was developed and silanized by treatment with (tridecafluoro-1,1,2,2-tetrahydrooctyl)trichlorosilane vapor (Gelest, Inc) in a vacuum chamber at 20° C. to reduce surface adhesion. Polydimethylsiloxane (PDMS, Dow Corning) was mixed in the ratio 10:1, degassed, and poured to a depth of 5 mm onto the silanized wafer contained in a 9 cm petri dish. The PDMS was cured for 3 hours at 65° C., excised, peeled off the wafer, and trimmed to size. Inlet port 125 and outlet port 130 were formed using a 1.5 mm diameter punch. For bonding, the PDMS block 105 (microfluidic chip) and glass slide 110 (backing) were cleaned and activated by placing both parts in an air plasma (medium field strength, PDC-32G plasma cleaner, Harrick Plasma, Inc., USA) for 1 minute and immediately bringing the glass slide into contact with the feature side of the PDMS microfluidic chip 105. Care was taken to ensure that the recording channel contacted all three electrodes on the glass slide. Curing of the bond was accelerated by baking the device for 30 minutes at 100° C. See FIG. 1.

TABLE 1

Dimensions of Exemplary Microfluidic Device of FIG. 1

| Feature | Width (mm) Top view x-dimension | Length (mm) Top view y-dimension | Depth (mm) |
|---|---|---|---|
| Inlet port (125) | 1.5 (diam) | 1.5 (diam) | 5 |
| Outlet port (130) | 1.5 (diam) | 1.5 (diam) | 5 |
| Holding reservoir (115) | 11 | 19.1 | 0.1 |
| Recording channel (120) | 0.3 | 17.5 | 0.1 |
| Chip (PDMS block) (105) | 14 | 45 | 5 |

The overall dimensions of the exemplary microfluidic device of FIG. 1 include a width of 25 mm, a length of 75 mm and a depth of 6 mm. In embodiments provided herein is a microfluidic device for measuring a composite electropharyngeogram (EPG) signal from a pool of multiple nematodes comprising exemplary microfluidic chip 105. In embodiments, an exemplary microfluidic chip comprises an inlet port 125 and outlet port 130 directly connected to a holding reservoir 115; a single recording channel 120, configured to hold 10 to 10,000 nematodes, connected in series to the holding reservoir 115; and, two or more integrated electrodes 135 and 145 directly connected to the recording channel. In certain embodiments, the microfluidic chip 105 is attached to a backing 110 to form an exemplary microfluidic device.

Provided herein is an exemplary microfluidic system 200 for measuring a composite electropharyngeogram (EPG) signal from a pool of multiple nematodes comprising exemplary microfluidic device 100 and a recording dock 205 and differential amplifier 210. In certain embodiments, the system further comprises a frame that holds the microfluidic device 100, which is then placed in the recording dock 205.

Example 2: Methods of Measuring and Recording a Composite Electropharyngeogram (EPG) Signal from a Pool of Multiple Nematodes Using the Device of Example 1

Provided herein is a method for measuring and recording a composite electropharyngeogram (EPG) signal from a pool of multiple nematodes using the microfluidic device 200 of FIG. 2 featuring a microfluidic device 100, a recording dock 205, and a differential amplifier 210.

To obtain nematodes of a consistent size that were compatible with the dimensions of the recording channel 120, we utilized a common procedure to obtain a large number of age synchronized eggs. This involved dissolving gravid hermaphrodites in a bleaching solution the ingredients of which are shown in Table 2. Eggs were deposited in a culture plate containing food and cultivated at 20 C for 3 days, yielding a large population of young adult nematodes.

TABLE 2

Bleaching Solution

| Constituent | Amount (mL) |
|---|---|
| Distilled water | 3.675 |
| Sodium hypochlorite solution (5%) | 1.200 |
| NaOH solution (10M) | 0.125 |

To prepare nematodes for recording, 2 mL of "normal M9 buffer solution," defined in Table 3, was added to a culture plate containing young adult nematodes grown from synchronized eggs. The plate was swirled to lift nematodes into the solution and the contents were poured into a 2 mL Eppendorf tube. Nematodes were cleaned of adherent bacteria and debris by 5 cleaning cycles each of which involved pelleting nematodes in a centrifuge (1.2 g, 30 sec), drawing off the supernatant, and resuspending in M9 buffer. To stimulate pharyngeal pumping, the final resuspension used "serotonin M9 buffer solution" which contained 10 mM serotonin in addition to the constituents in Table 3.

TABLE 3

M9 Buffer Solution

| Constituent | Amount |
| --- | --- |
| $KH_2PO_4$ | 3 g |
| $Na_2HPO_4$ | 6 g |
| NaCl | 5 g |
| $MgSO_4$ (1M) | 1 mL |
| Distilled water | to 1 L |

For filling the microfluidic device, a 5 mL syringe was fitted with a 50 cm length of polyethylene tubing (1.4 mm ID, 1.9 mm OD), with a stainless-steel tube (1.2 mm ID, 1.47 mm OD, 12.7 mm long) inserted halfway into the open end of the tubing to facilitate connection with the inlet port of the device. The syringe and tubing were filled with serotonin M9 buffer which was injected into the inlet port 125 until solution began to escape from the outlet port 130 and filling the reservoir 115. For transferring nematodes into the microfluidic device, approximately 10 uL of fluid from the pellet of nematodes in an Eppendorf tube was drawn into the tube of a second syringe, prepared in the same manner as the first syringe, then injected into the inlet port 125. The microfluidic device was placed in a 50 mL centrifuge tube and spun for at 420 g for 5 min, packing nematodes into in the recording channel 120. This procedure yielded approximately 25 nematodes between electrodes 135 and 145. The microfluidic device was inserted into a recording dock 205 thereby connecting it to a differential amplifier 210 (ScreenChip System, NemaMetrix, Inc.) which amplified the voltage difference between electrodes 135 and 145. The third electrode 140 served as a ground electrode to reduce electrical noise.

Figure 3A:
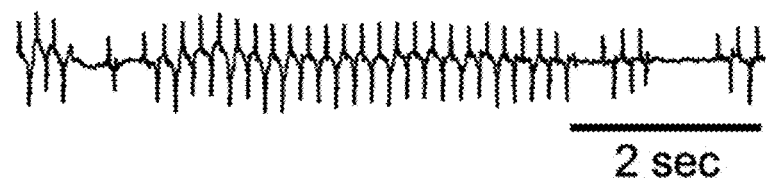
FIGS. 3A, 3B and 3C show recordings of EPG measurements from individual nematodes.
Figure 3B:
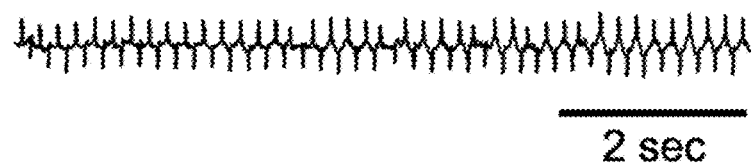
Figure 3C:
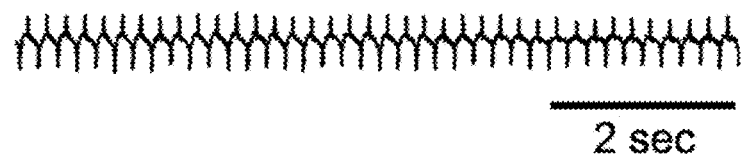
Figure 3D:
FIG. 3D shows an in silico composite EPG recording from 22 individual nematode EPG measurements.
Figure 3E:
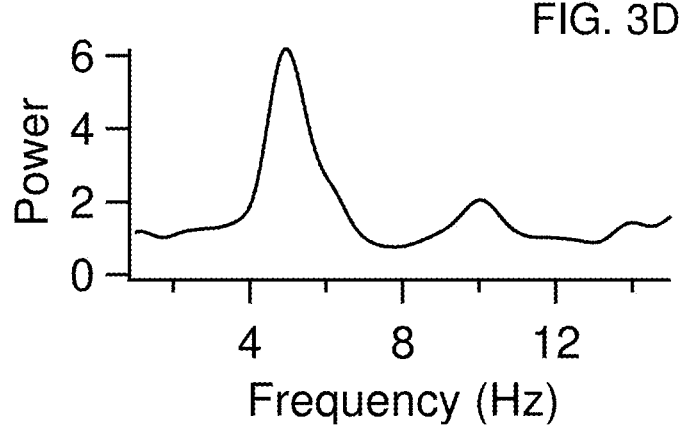
FIG. 3E shows a power spectrum for the in silico composite EPG recording, using the microfluidic device 100.

According to circuit theory, (i) the waveform of a composite EPG recorded at electrodes 135 and 145 should be the sum of the voltage differences generated by each nematode at its unique location and orientation with respect to the electrodes and other nematodes, and (ii) the peak frequency of the waveform's power spectrum should represent the average pumping frequency of the population of nematodes between the electrodes. We validated this theory by recording single-nematode EPGs from 22 nematodes in serotonin M9 buffer solution for 10-14 min using a commercially available recording system (ScreenChip System, NemaMetrix, Inc.). See U.S. Pat. No. 9,723,817. Segments of three of the individual 22 nematode EPG recordings are shown in FIG. 3A-C. The average pumping frequency of the 22 nematodes was 4.9±0.13 Hz (SEM). FIG. 3D shows a portion of the synthetic (in silico) composite EPG recording which was computed by taking the sum of all 22 single-nematode EPG measurements. This recording shows periods of synchronous, high amplitude activity (indicated by horizontal lines) alternating with periods of asynchronous, low amplitude activity. This is the waveform envelope expected for a population of oscillators operating at similar but unique frequencies such that they periodically come in and out of phase, a phenomenon commonly referred to as "beating". The power spectrum of this recording had a peak frequency of 5.1 Hz (FIG. 3E), which agrees well with the average pumping frequency of the 22 single-nematode EPG recordings.

Figure 4A:
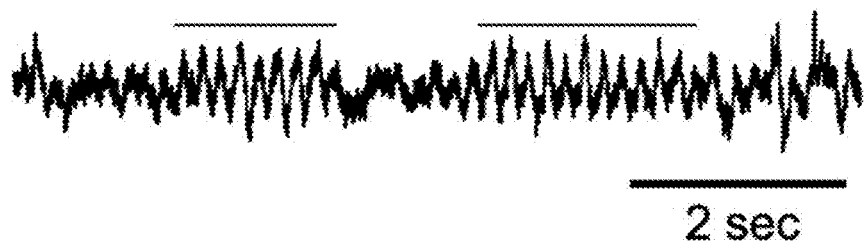
FIGS. 4A-4C show recordings of EPG measurements from a pool of multiple nematodes in M9 buffer with serotonin (FIG. 4A); M9 buffer without serotonin (FIG. 4B); and, a power spectrum of the EPG measurements from a pool of multiple nematodes (FIG. 4C), using the microfluidic device 100.
Figure 4B:
Figure 4C:
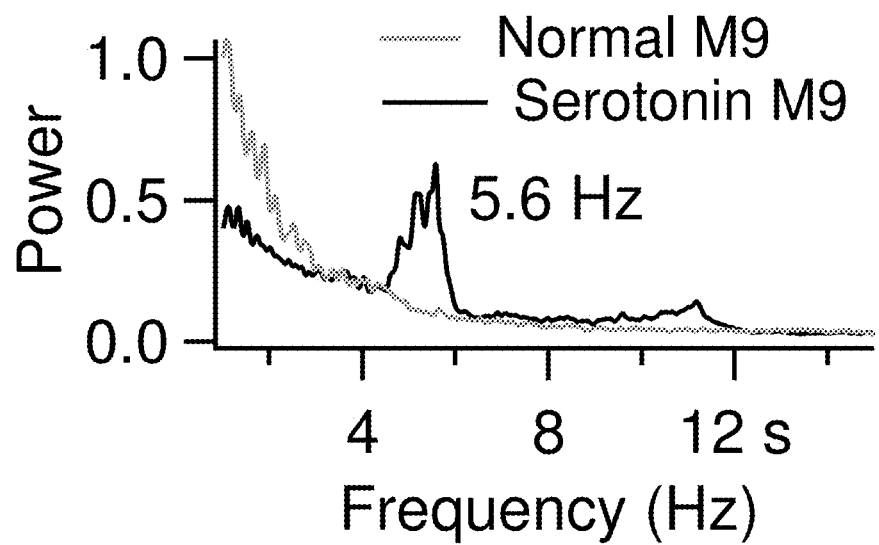

FIG. 4A shows a multi-nematode (composite) EPG recorded in serotonin M9 buffer solution from a pool of multiple nematodes utilizing microfluidic system 200. Two lines of evidence indicate that the recorded activity represents pharyngeal pumping. First, the envelope of this trace strongly resembles the envelope of the synthetic composite EPG recording in FIG. 3D in that it also exhibits periods of synchronous, high amplitude activity (indicated by horizontal lines) alternating with periods of asynchronous, low amplitude activity. No such envelope was observed in the voltage trace recorded in normal M9 buffer without serotonin to stimulate pharyngeal pumping (FIG. 4B), a condition in which there should be little or no pumping. Second, the power spectrum of recorded activity had a prominent peak at 5.6 Hz (FIG. 4C), in agreement with the pumping frequency of single nematodes exposed to the saturating concentration of serotonin used in this experiment, and the fact that this peak was absent in power spectrum of the voltage trace recorded in normal M9 buffer solution.

Example 3: Design and Fabrication of Microfluidic Device (500)

Provided herein is a microfluidic device and system for measuring and recording a composite electropharyngeogram (EPG) signal from a pool of multiple nematodes. See FIGS. 5 and 6.

Provided herein is the design and fabrication of the microfluidic device 500 and system 600 represented in FIGS. 5 and 6. The microfluidic device was prepared with a rectangular block (e.g. microfluidic chip) 505 composed of polydimethylsiloxane (PDMS) measuring 45 mm×14 mm×5 mm bonded to a 1 mm thick glass microscope slide (e.g. backing) 510 measuring 75 mm×25 mm. A single fluidic feature was molded into the bottom of the block: a recording channel 515 measuring 90 μm high, 300 μm wide, and 20 mm long. The channel was connected to a 1.5 mm diameter inlet port 520, and 1.5 mm diameter outlet port 525. Two stainless-steel tubes 530 and 535 measuring, 1.5 mm (diameter)×12.5 mm were inserted into the PDMS block 505 to form inlet 520 and outlet 525 connections, respectively. The opening of the stainless-steel tube 535 within the PDMS was covered by a nylon mesh 540 having square pores measuring 11 μm on a side. The channel was filled with an aqueous buffer solution. The stainless-steel tubes 530, 535 contacted the aqueous solution such that they also served as electrodes.

The microfluidic device 500 was fabricated in the same manner as the device 100 except that the 3-inch silicon wafer was spin coated with SU8-2075 photoresist (Microchem Corp.) at 2559 revolutions per minute (RPM) to obtain a height of 90 μm.

TABLE 4

Dimensions of the Exemplary Microfluidic Device 500 of FIG. 5

| Feature | Width (mm) Top view x-dimension | Length (mm) Top view y-dimension | Depth (mm) |
| --- | --- | --- | --- |
| Inlet port (520) | 1-2 (diam) | 1-2 (diam) | 5 |
| Outlet port (525) | 1-2 (diam) | 1-2 (diam) | 5 |
| Stainless-steel tubes (530, 535) | 1-2 (diam) | 1-2 (diam) | 12.5 |
| Recording channel (515) | 0.01-1 | 5-500 | 0.01-0.30 |
| Chip (PDMS block) (505) | 20-60 | 25-160 | 1-10 |

The overall dimensions of the exemplary microfluidic device of FIG. 5 comprises a width of 25 mm, a length of 75 mm and a depth of 6 mm. In embodiments provided herein is a microfluidic device for measuring a composite electropharyngeogram (EPG) signal from a pool of multiple nematodes comprising exemplary microfluidic chip 505. In embodiments, an exemplary microfluidic chip comprises an inlet port 520 and outlet port 525 directly connected to a single recording channel 515, configured to hold 10 to 10,000 nematodes and two or more stainless-steel tubes 530 and 535 directly connected to the recording channel via the inlet and outlet port 520, 525. In certain embodiments, the microfluidic chip 505 is attached to a backing 510 to form an exemplary microfluidic device.

Provided herein is an exemplary microfluidic system 600 of FIG. 6 for measuring a composite electropharyngeogram (EPG) signal from a pool of multiple nematodes comprising exemplary microfluidic device 500, differential amplifier 210, amplifier cable 605 fitted with clips 610 to connect the amplifier to the microfluidic device 500, and a platform 615 which anchors the cable 605 and clips 610, and has a hole 620 in the center so the device 500 can be viewed under transillumination on a conventional stereomicroscope.

Example 4: Methods of Measuring and Recording a Composite Electropharyngeogram (EPG) Signal from a Pool of Multiple Nematodes Using the Device of Example 3

Provided herein is a method for measuring and recording a composite electropharyngeogram (EPG) signal from a pool of multiple nematodes using the microfluidic system 600 of FIG. 6 featuring a microfluidic device 500, differential amplifier 210, amplifier cable 605 fitted with clips 610, for example micro test lead hooks, to connect the amplifier to the microfluidic device 500.

To obtain nematodes of a consistent size that were compatible with the dimensions of the recording channel 515, we used the method of Example 2. Alternative methods using filters can also be used to obtain an age/size synchronized population of nematodes for use. See US Patent Publ. No. 2019/0090458.

To prepare nematodes for recording, we used the method of Example 2, except that the final resuspension used "normal M9 buffer solution," defined in Table 3.

For filling the microfluidic device, we used the method of Example 2, except that the syringe and tubing were filled with "normal M9 buffer solution."

Figure 7A:
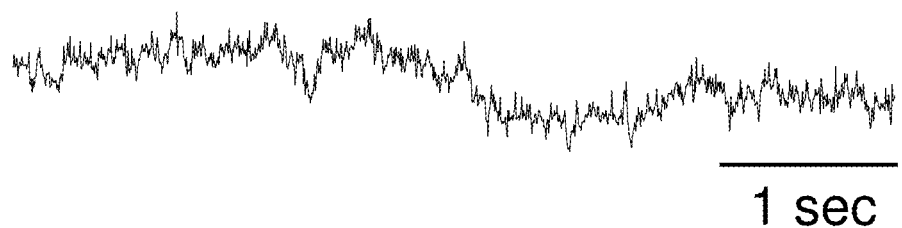
FIG. 7A-7C shows recordings of EPG measurements from a pool of multiple nematodes in M9 buffer without serotonin (FIG. 7A); M9 buffer with serotonin (FIG. 7B); and, power spectra of the EPG measurements from the pool of multiple nematodes recorded in FIGS. 7A and 7B (FIG. 7C), using the microfluidic device 500.

FIG. 7A shows a typical segment of a multi-nematode (composite) EPG recorded for 16 minutes in Solution A, normal M9 buffer solution, from a pool of multiple nematodes utilizing microfluidic system 600. At the end of this recording, the normal M9 buffer solution was replaced with Solution B, serotonin M9 buffer solution disclosed in Example 1, without dislodging the original pool of nematodes. Replacement was accomplished by exchanging the syringe and tubing filled with normal M9 buffer solution for a syringe and tubing filled with serotonin M9 buffer solution. Gentle pressure was applied to the syringe until approximately 5 µL of fluid flowed out of the outlet port, corresponding to approximately 10 times the volume of the recording channel. The nylon mesh 540 covering the opening of the stainless-steel tube 535 within the PDMS block 505 prevented the nematodes from leaving the recording channel while the fluid was exchanged.

Figure 7B:
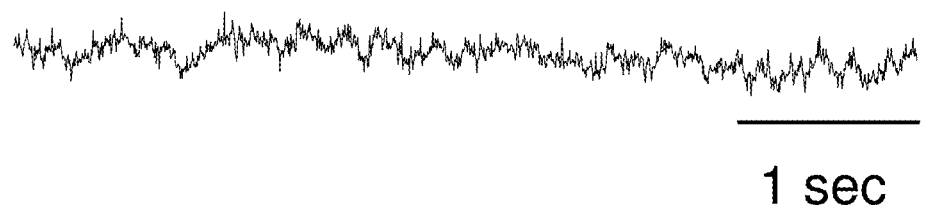
Figure 7C:
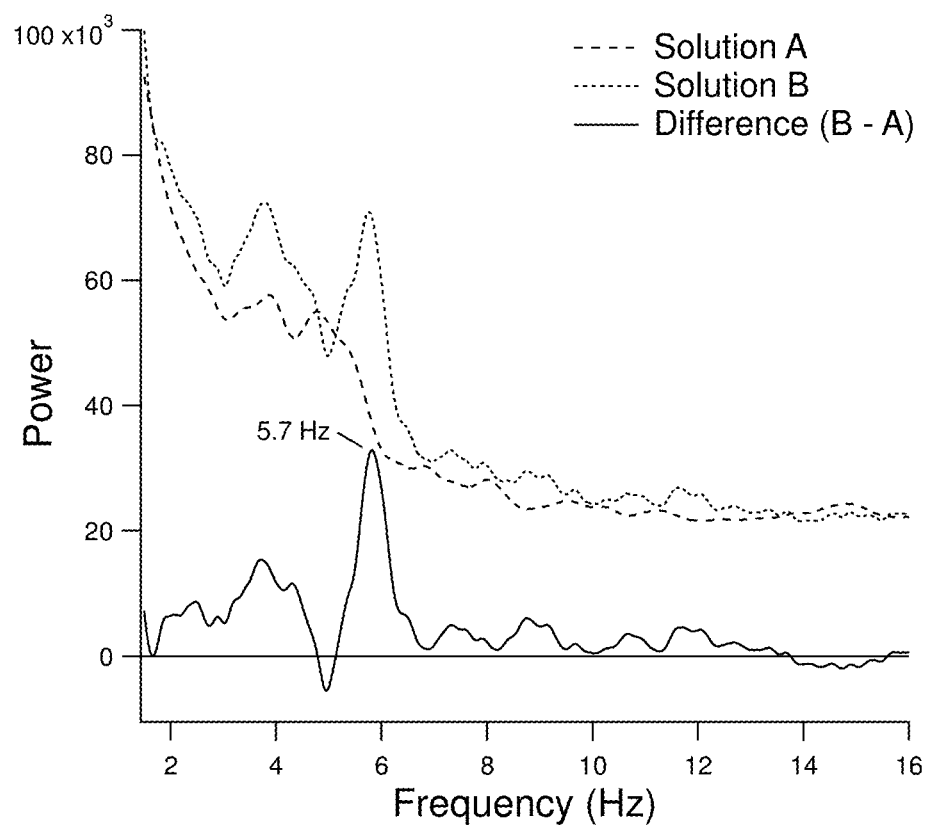

FIG. 7B shows a typical segment of a multi-nematode (composite) EPG recorded for 25 minutes in Solution B from the same pool of multiple nematodes recorded in FIG. 7A, again utilizing the microfluidic system 600. FIG. 7C shows the power spectrum of the recordings obtained in Solution A and Solution B, together with a third trace showing the difference between the first two traces. The difference trace revealed a prominent peak centered at 5 Hz, which indicates the specific effect of serotonin on the power spectrum. The center frequency of this peak is within the expected range of pharyngeal pumping frequency. This result, like the result illustrated in FIG. 4C, confirms that the recorded activity corresponds to pharyngeal function. However, as the same population of nematodes was recorded under conditions of the two different buffer solutions in FIG. 7C, but not in FIG. 4C, FIG. 7C establishes, in addition, that the system 600 can be used to measure the effect of drugs or other test compounds on pharyngeal pumping. This finding is significant because it establishes the feasibility of an "A versus B" experimental design, a widely used screening approach in which the effects of the drug in Solution B are obtained by comparison with an internal control, here solution A, applied to the same pool or set of test organisms.

Importantly, the use of the A versus B experimental design is not limited to measuring the effect of drugs like serotonin, which directly induces pharyngeal pumping. This design can also be used to measure the effect of a drug or other test compound that modulates pharyngeal pumping frequency only after it has already been initiated. For example, this could be done by measuring the difference in average pumping frequency in solutions A and B, where solution A is serotonin M9 buffer solution, and solution B is serotonin M9 buffer solution plus a test compound such as an anthelmintic. In another example, this could be done by subtracting the power spectra of the recordings obtained in solutions A and B where, again, where solution A is serotonin M9 buffer solution, and solution B is serotonin M9 buffer solution plus a test compound such as an anthelmintic.

What I claim is:

1. A microfluidic system for recording a composite electropharyngeogram (EPG) signal from a pool of multiple nematodes comprising:
   a) an inlet port and outlet port directly connected to a holding reservoir;
   b) a single recording channel, configured to hold 10 to 10,000 nematodes, connected in series to the holding reservoir;
   c) two or more integrated electrodes directly connected to the recording channel; and,
   d) at least one differential amplifier or at least one voltage-clamp amplifier, wherein the amplifier is connected to an output from the two or more integrated electrodes.

2. A method for recording a composite electropharyngeogram (EPG) signal from a pool of multiple nematodes comprising:
   a) introducing the pool of multiple nematodes into the holding reservoir through the inlet port of the microfluidic system of claim 1, wherein the pool of multiple nematodes is present in an aqueous buffer solution;
   b) moving the pool of multiple nematodes into the single recording channel;
   c) measuring electrophysiological signals from the pool of multiple nematodes; and,
   d) recording the electrophysiological signals as a single composite EPG.

3. The method of claim 2, wherein the buffer solution comprises serotonin, food, or other stimulant to cause pharyngeal pumping.

4. The method of claim 2, wherein the pool of nematodes comprises transgenic nematodes or transgenic nematodes comprising a gene variant.

5. The method of claim 2, wherein the moving the pool of multiple nematodes into the single recording channel comprises applying a vacuum, positive pressure, or centrifugal force to the system.

6. A microfluidic device for measuring a composite electropharyngeogram (EPG) signal from a pool of multiple nematodes comprising:
   a) an inlet port and outlet port directly connected to a single recording channel;
   b) the single recording channel, configured to hold 10 to 10,000 nematodes;
   c) a tube placed in each of the inlet port and outlet port, wherein the tube placed in the outlet port comprises a filter to retain nematodes in the single recording channel; and,
   c) two or more electrodes connected to the recording channel.

7. A microfluidic system for recording a composite electropharyngeogram (EPG) signal from a pool of multiple nematodes comprising the microfluidic device of claim 6, the system comprising:
   a) an inlet port and outlet port directly connected to a single recording channel;
   b) the single recording channel, configured to hold 10 to 10,000 nematodes;
   c) a tube placed in each of the inlet port and outlet port, wherein the tube placed in the outlet port comprises a filter to retain nematodes in the single recording channel;
   d) two or more electrodes connected to the recording channel; and,
   e) at least one differential amplifier or at least one voltage-clamp amplifier, wherein the amplifier is connected to an output from the two or more electrodes.

8. A method for recording a composite electropharyngeogram (EPG) signal from a pool of multiple nematodes comprising:
   a) introducing the pool of multiple nematodes into the single recording channel through the inlet port of the microfluidic system of claim 7, wherein the pool of multiple nematodes is present in an aqueous buffer solution;
   b) measuring electrophysiological signals from the pool of multiple nematodes; and,
   c) recording the electrophysiological signals as a single composite EPG.

* * * * *